United States Patent
Aleisa et al.

(10) Patent No.: US 9,207,199 B2
(45) Date of Patent: Dec. 8, 2015

(54) ANALYZER FOR MONITORING SALT CONTENT IN HIGH RESISTIVITY FLUIDS

(71) Applicant: Saudi Arabian Oil Company, Dhahran (SA)

(72) Inventors: Rashed Mohammad Aleisa, Dhahran (SA); Naim Akmal, Dhahran (SA); Taher Ali Atef Alamri, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 167 days.

(21) Appl. No.: 14/145,258

(22) Filed: Dec. 31, 2013

(65) Prior Publication Data

US 2015/0185174 A1 Jul. 2, 2015

(51) Int. Cl.
| | |
|---|---|
| *G01N 27/06* | (2006.01) |
| *G01N 33/28* | (2006.01) |
| *G01N 33/22* | (2006.01) |
| *G01N 27/416* | (2006.01) |
| *G01N 27/38* | (2006.01) |

(52) U.S. Cl.
CPC ............ *G01N 27/06* (2013.01); *G01N 27/4166* (2013.01); *G01N 33/22* (2013.01); *G01N 33/28* (2013.01); *G01N 33/2835* (2013.01); *G01N 27/38* (2013.01)

(58) Field of Classification Search
CPC ....... G01N 27/06; G01N 33/28; G01N 33/22; G01N 27/26; G01N 27/327; G01N 33/50
USPC .............................. 324/698; 204/247.2, 400; 205/775–794.5; 422/68.1, 82.01–82.04
See application file for complete search history.

(56) References Cited

U.S. PATENT DOCUMENTS

| | | | |
|---|---|---|---|
| 3,181,058 A | 4/1965 | Gulbrandsen | |
| 4,684,457 A | 8/1987 | McKechnie et al. | |
| 4,838,999 A * | 6/1989 | Haar et al. | 205/781.5 |
| 5,489,371 A | 2/1996 | Joseph et al. | |
| 5,746,908 A | 5/1998 | Mitchell | |
| 2004/0084328 A1* | 5/2004 | Jones et al. | 205/790 |
| 2009/0159462 A1 | 6/2009 | Zizek | |

OTHER PUBLICATIONS

International Search Report and Written Opinion dated Mar. 23, 2015 pertaining International Patent Application PCT/US2014/068043.

(Continued)

*Primary Examiner* — Tung X Nguyen
*Assistant Examiner* — Zannatul Ferdous
(74) *Attorney, Agent, or Firm* — Dinsmore & Shohl LLP

(57) ABSTRACT

An electrochemical polymerization based salt content analyzer configured to determine salt composition in a direct, fast, and serial manner. The salt content analyzer includes three electrodes: a working electrode, a counter electrode and a reference electrode. In operation, the current passing through the electrodes as a sweeping voltage is applied may be analyzed to determine the salt content of the analyte. When a voltage is applied, an electro-polymerizable monomer forms a thin film on the working electrode. The working electrode includes an access control mechanism to only expose a fraction of the working length of the working electrode to the outside environment at any given time. The access control mechanism is advanced between tests to expose a fresh portion of the working electrode and conceal the portion with a thin film of electro-polymerized monomer. Thus, testing may be performed in a serial manner.

20 Claims, 4 Drawing Sheets

(56) References Cited

OTHER PUBLICATIONS

Li, Q. et al.; A method for in situ auto-renewal of the surface of glassy carbon electrodes; Journal of Electroanalytical Chemistry; 2003; pp. 19-23; vol. 560; Elsevier B.V.

ASTM Designation: D3230-10; Standard Test Method for Salts in Crude Oil (Electrometric Method); 2012; vol. D3230; pp. 1-7; ASTM Interntional.

* cited by examiner

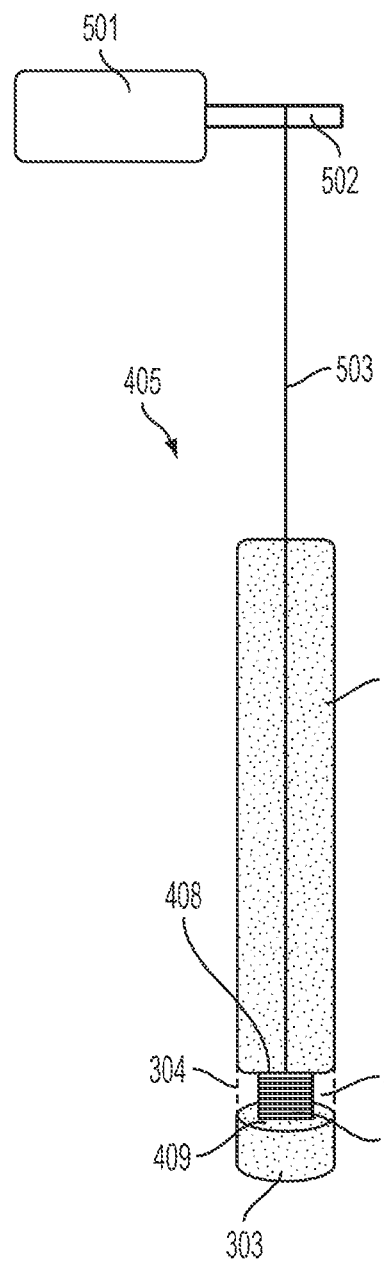
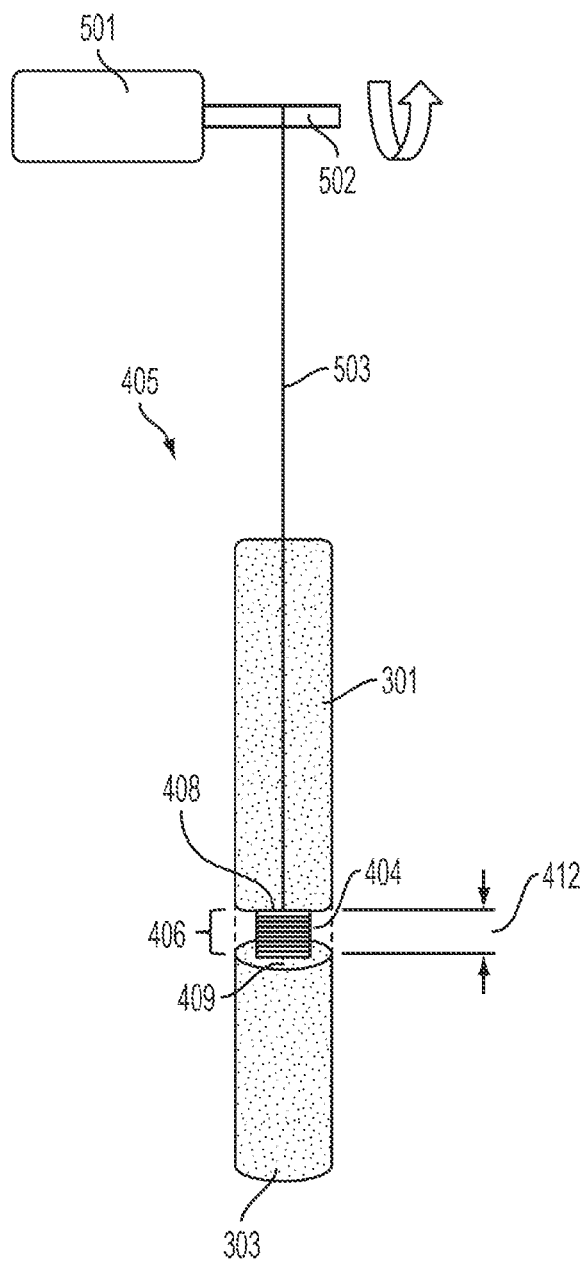
FIG. 1A
FIG. 1B

ANALYZER FOR MONITORING SALT CONTENT IN HIGH RESISTIVITY FLUIDS

BACKGROUND

1. Field

The present specification generally relates to monitoring salt content in process fluids and, more particularly, to monitoring salt content in high resistivity fluids such as crude oil, paraffin oil, gasoline, and diesel fuel.

2. Technical Background

Salts present in crude oil are preferably removed before or during the refining process. Additionally, monitoring of the salinity of crude oil during the refining process is desirable to determine the effectiveness of the removal process. The amount of salt present in crude oil is a significant factor that may lead to several problems encountered during transporting and refining processes, including fouling, deactivation of catalysts and severe corrosion in pipelines. In essence, presence of salt in crude oil, even at parts per million levels, may cause major damage during the refining process. Thus, a desalting process is a standard operation in the overall refining process of crude oil into various products. Therefore, it is desirable to determine the content of salt in crude oil at, for example, the desalting process in real-time to verify salt is being effectively removed.

The salt content in a given sample of crude oil depends mostly on the source of the crude oil. Specifically, different wells and different types of oil fields exhibit varying salt content. Additionally, the residual salt water in shipment tankers can contaminate the crude oil with salt. In most cases, the salt content of the crude oil consists of salt dissolved in small droplets of water that are dispersed in the crude oil. The chemical composition may also vary, but mostly the sodium chloride is considered as the main source with lesser degree of calcium and magnesium chlorides.

Measurement of salt in crude oil is a major procedure in petroleum industry operations during transportation, refining, processing and production. The need for fast and reliable system of measurement of salt levels is desirable in a desalting process. An analyzer must not only be reliable but must also provide such measurements in adequate time. Existing analyzers developed to determine salt content in crude oil and similar moieties are based on measurement of electrical properties of the crude oil. Specifically, existing analyzers are dependent on conducting electrochemical tests to detect the electroactive species of the analyte (e.g., crude oil) by measuring the conductance of the material. They contain conductive electrodes that are placed in flowing crude oil sample to measure the difference in potential and, thereby, to determine the salinity value. However, such techniques suffer several limitations, including corrosion, precipitation on electrodes, temperature restriction, short lifespan and accuracy of data at low levels (e.g. parts per million). Corrosion may occur due to presence of conductive-metal on both electrodes, and water present in the analyte flow combined with salts. The salt also precipitates on the surface of these electrodes and causes deterioration of the electrode surface, leading to poor durability and reliability of the sensing system. Moreover, conductivity changes when the operating temperature is varied during the analysis, which changes the resulting salinity values in the obtained samples of crude oil.

Efforts have been made to develop a real-time technique to measure salt present in crude oil based on the ASTM methods of crude oil salinity measurement using potentiometric and electrometric techniques. However, the American Standard Test Methods (D 3230 & D 6470) encounter disadvantages and limitations. For example, ASTM D 3230 is an electrometric method that obligates extensive sample preparation with numerous solvents usage such as xylene, butanol, and methyl alcohol. Similarly ASTM D 6470, which is a potentiometric technique, requires extensive preparation. The extensive preparation limits the usability of both methods if fast and immediate results are needed. Robustness, durability, and fast results are desirable for real-time measurement of salt present in crude oil or similar complexes.

SUMMARY

According to various embodiments, salt content analyzers that perform multiple sequential determinations of a salt content of an analyte in a test fluid containing the analyte and an electro-polymerizable monomer without requiring intermediate cleaning or polishing of a working electrode between determinations are provided. The salt content analyzers may include an analysis vessel that accommodates the test fluid, a counter electrode, and a reference electrode. The salt content analyzers may also include a working electrode assembly comprising the working electrode and an access control mechanism, the working electrode assembly being immersible in the test fluid. The salt content analyzers may further include a voltage source that applies an electrical potential to the working electrode and a measurement apparatus that measures an electrical current passed between the working electrode and the counter electrode when the electrical potential is applied to the working electrode. The working electrode and the counter electrode form an electrochemical cell. The access control mechanism of the working electrode assembly may include a movable barrier that exposes a measuring portion of the working electrode to the test fluid through an access gap and forms a fluid tight seal around a covered portion of the working electrode, the fluid tight seal preventing exposure of the covered portion to the test fluid. During a single determination of the analyte in the test fluid, electropolymerization of the electro-polymerizable monomer occurs at the measuring portion of the working electrode and a polymer film is deposited onto the measuring portion to form a used measuring portion. After the single determination, movement of the movable barrier exposes a fresh measuring portion of the working electrode for use in a subsequent determination without requiring intermediate cleaning or polishing of the working electrode and forms a fluid tight seal around the used measuring portion formed during the single determination.

According to further embodiments, methods of performing multiple sequential determinations of salt content in a petroleum product without intermediate cleaning or polishing of a working electrode between determinations are provided. The methods may include providing a salt content analyzer having an analysis vessel, a working electrode assembly including a working electrode and an access control mechanism, a voltage source, and a measurement apparatus. The access control mechanism of the working electrode assembly may include a movable barrier that exposes a measuring portion of the working electrode through an access gap to a test fluid containing the petroleum product in the analysis vessel and forms a fluid tight seal around a covered portion of the working electrode, the fluid tight seal preventing exposure of the covered portion to the test fluid. The methods may further include mixing the petroleum product and a homogenous mixture to the analysis vessel to form a test fluid, the homogeneous mixture including water, at least one conductivity solvent, and at least one electro-polymerizable monomer. A sweeping potential may be applied with the voltage source to the working electrode in the test fluid to generate an electric current from a counter electrode in the test fluid to the working electrode, whereby electropolymerization of the electro-polymerizable monomer occurs at the measuring portion of the working electrode and a polymer film is deposited onto the measuring portion to form a used measuring portion. A peak current generated during the application of the sweeping potential may be recorded with the measurement apparatus. The methods may further include comparing the peak current with a predetermined calibration curve to determine the salt content of the petroleum product. The methods may further include moving the movable barrier of the access control mechanism to cover the used measuring portion of the working electrode and to expose a fresh measuring portion of the working electrode for use in a subsequent determination.

Additional features and advantages of the embodiments described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

FIG. 1A is a schematic representation of a working electrode of a salt content analyzer with an access control mechanism positioned for a first analysis, according to embodiments described herein;

FIG. 1B is a schematic representation of a working electrode of a salt content analyzer with the access control mechanism positioned differently to uncover a fresh access area after the first analysis using the working electrode having the access control mechanism positioned as in FIG. 1A, according to embodiments described herein;

DETAILED DESCRIPTION

Figure 2:
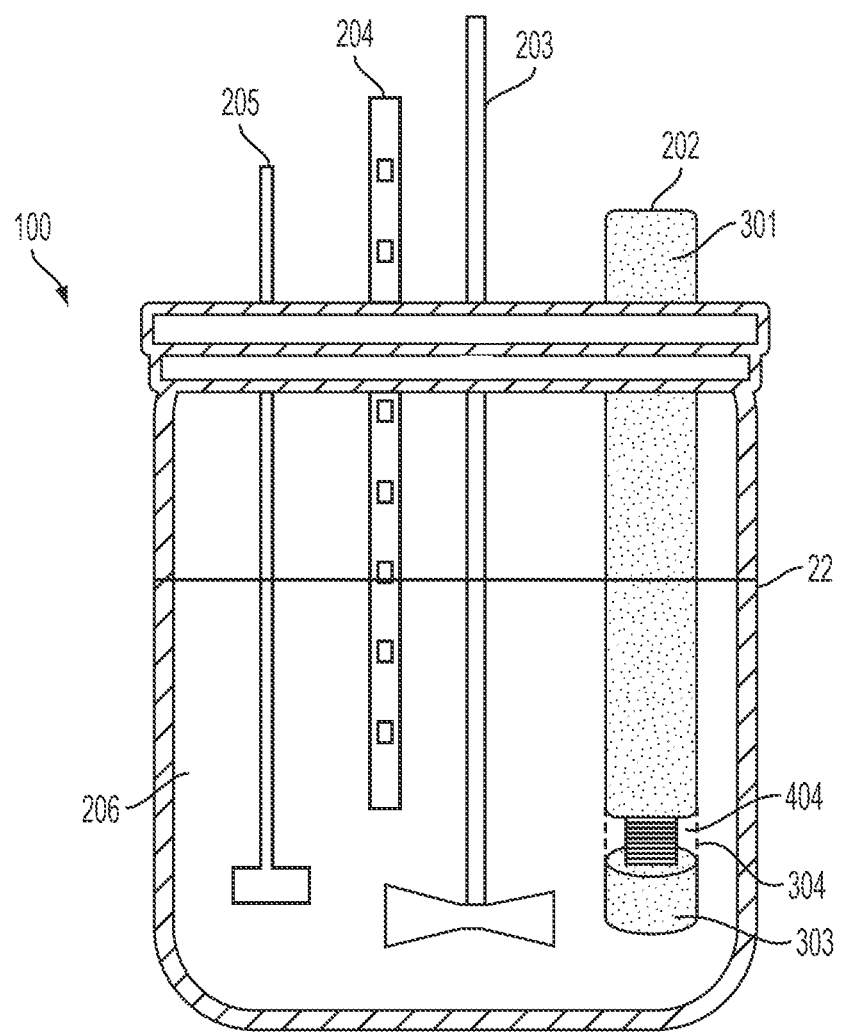
FIG. 2 is a schematic representation of an analysis vessel and electrodes of a salt content analyzer, according to embodiments described herein.

Embodiments of a salt content analyzer 100 will now be described with reference to FIGS. 1-3. The salt content analyzer 100 is an electrochemical polymerization based analyzer capable of determining salt contents of multiple test fluids containing high resistivity complexes such as crude oil, paraffin oil, gasoline, and diesel fuel without a need to clean or polish a working electrode between each determination.

The salt content analyzer 100 determines salt content of the high resistivity complexes based on principles of electrochemical polymerization. Electro-polymerizable monomers form a polymer upon application of an electrical potential. When potential is applied across the two electrodes, an extremely thin film of electro-polymerized monomer is deposited on one electrode. The film formation is dependent on the amount of electrolytes present in the matrix. Once the potential is applied, the quantity of polymer formed is directly proportional to the amount of electrolyte present in the media, which for present purposes is the quantity of salt in the analyte. Therefore, salts present in crude oil, paraffin oil, gasoline, diesel fuel, and other fluids with high electrical resistivity analytical matrices can be measured by computing the rate of polymerization based on the applied potential versus produced current. For purposes of this disclosure, the threshold of high resistivity (low conductivity) is commensurate with that of crude oil at or above 1.5 $\Omega\cdot cm$. It is noted that the threshold is an approximate value because resistivity of crude oil is sensitive to metals, salts, and other materials dispersed in the crude oil. Additionally, the range of general hydrocarbon mixtures such as gasoline, diesel, kerosene, etc., is included within the range of high resistivity fluid.

The salt content analyzer 100 includes an analysis vessel 22 that accommodates a test fluid, a counter electrode 205, and a reference electrode 204. A working electrode assembly of the salt content analyzer 100 may include a working electrode 202 and an access control mechanism 405. An electro-polymerizable monomer supply 27 may be connected to the analysis vessel 22 and may provide an electro-polymerizable monomer to the analysis vessel 22. Thus, the salt content analyzer 100 may be configured as an electrochemical cell having three electrodes. Specifically, the three electrodes are the working electrode 202, the counter electrode 205 and the reference electrode 204. During a determination of an analyte, the counter electrode 205, the working electrode 202, and the reference electrode 204 are disposed in the analysis.

The working electrode 202 is partially covered by the access control mechanism 405. The access control mechanism 405 may be or may include a movable barrier that defines an access gap 406 though which only a portion of a measuring surface of the working electrode 202 is exposed to test fluid 206 in the analysis vessel 22 during a discrete measurement time interval. The access control mechanism 405 forms a fluid tight seal 408, 409 with the working electrode 202 at each end of the access gap 406 such that only a fraction of the working electrode 202 surface is exposed to the test fluid 206 in the analysis vessel 22. The exposed surface of the working electrode 202 defined by the access gap 406 is the access area 404. In illustrative embodiments, the surface area of the access area 404 during any one determination of salt content in the test fluid 206 can be from about 1% to about 50% of the total surface area of the working electrode 202. In various embodiments, the access area 404 may be approximately 20% of the total surface area of the working electrode 202 approximately 10% of the total surface area of the working electrode 202, approximately 5% of the total surface area of the working electrode 202, or approximately 1% of the total surface area of the working electrode 202. In an illustrative embodiment, the access area 404 is approximately 0.5 mm in length such that 0.5 mm of the total length of the working electrode 202 is exposed. In further illustrative embodiments the length 412 of the access area 404 may be about 0.25 mm, about 1 mm, about 5 mm, or about 10 mm, for example. The total length of the working electrode 202 is dependent on the run-time cycle of the sensor. The longer period of time the working electrode 202 is desired to be utilized between downtime and cleaning the longer the working electrode 202 must be in length. Working electrodes 202 configured for nonstop operation for 1 month are envisioned. Working electrodes 202 of approximately 125 mm are specifically envisioned. Additional non-limiting lengths of the working electrode 202 include approximately 25 mm, approximately 50 mm, approximately 100 mm, approximately 200 mm, and approximately 500 mm.

In various embodiments, the working electrode assembly of the salt content analyzer 100 may include exposure of 0.5 cm$^2$ of the working electrode 202, 1 cm$^2$ of the working electrode 202, 1.5 cm$^2$ of the working electrode 202, 2 cm$^2$ of the working electrode 202, 5 cm$^2$ of the working electrode 202, or 10 cm$^2$ of the working electrode 202 by the access control mechanism 405 at any specific point in time.

In an embodiment, the access control mechanism 405 may include two distinct compartments or sleeves. Referring to FIG. 2, the two sleeves may include a first sleeve 301 and a second sleeve 303 which cover portions on opposite ends of the working electrode 202. The access area 404 is defined between the first sleeve 301 and the second sleeve 303. The access area 404 provides an access gap 406, through which the working electrode 202 is exposed to a test fluid 206 in the analysis vessel 22. In a further embodiment, the first sleeve 301 and second sleeve 303 may be connected to each other by access control wires 304 which exhibit corrosion and oxidation resistance, for example wires made of a noble metal. Non-limiting examples of access control wires 304 include wires made from platinum, gold, iridium, osmium, silver, palladium, rhodium, ruthenium, titanium, niobium, and tantalum. Connection of the first sleeve 301 and second sleeve 303 with the access control wires 304 maintains a constant access area 404 by virtue of maintenance of a constant access gap 406 between the first sleeve 301 and second sleeve 303.

In an embodiment, the first sleeve 301 and the second sleeve 303 may vary in length axially. As the access gap 406 shifts along the length of the working electrode 202, the first sleeve 301 is reduced in length and the second sleeve 303 is similarly extended in length while maintaining a constant access gap 406. The first sleeve 301 and the second sleeve 303 may vary axial length by, for example, stretching or contracting. The first sleeve 301 and the second sleeve 303 may also vary axial length by, for example, comprising a telescoping structure wherein a series of nested concentric elements are configured to extend from the nested configuration and extend in length to an extended configuration and similarly contract from the extended configuration into the nested configuration. Other telescoping structures are known to one having ordinary skill in the art and are equally contemplated.

In a further embodiment, the first sleeve 301 is a fixed length and the second sleeve 303 may vary in length. As the access gap 406 shifts along the length of the working electrode 202, the first sleeve 301 is extended beyond the working electrode 202 and the second sleeve 303 is extended in length while maintaining a constant access gap 406. The extension in length of the second sleeve 303, as the first sleeve 301 is removed from the working electrode 202, allows the second sleeve 303 to conceal the access area 404 from the previous analysis. Similarly, in a further embodiment, the second sleeve 303 is a fixed length and the first sleeve 301 may vary in length limited by the dimensions of the analysis vessel 22.

In an embodiment, shown in FIG. 1, the access control mechanism 405 is operated by a motor 501. The motor 501 may be an electric stepper motor including a permanent-magnet stepper motor or a variable-reluctance stepper motor for example. A the motor 501 operates, the motor head 502 rotates and in turn causes a sleeve advancing wire 503 to spool around the motor head 502. As the sleeve advancing wire 503 spools around the motor head 502 the free length of the sleeve advancing wire 503 is reduced and the end affixed to the first sleeve 301 is retracted. Retraction of the sleeve advancing wire 503 thus advances the first sleeve 301 along the length of the working electrode 202 and by virtue of the constant access gap 406 maintained by the access control wires 304 the second sleeve 303 also is advanced along the length of the working electrode.

In an embodiment, the sleeve advancing wire 503 is affixed at the end of the first sleeve 301 proximal the access gap 406. In a further embodiment, the sleeve advancing wire 503 is affixed to the first sleeve 301 near the end of the first sleeve 301 proximal the access gap 406. For purposes of this disclosure, non-limiting examples of near the end of the first sleeve 301 are within approximately 0.25, within approximately 0.5, within approximately 1, within approximately 2, or within approximately 5 times the length of the access area 404 of the end of the first sleeve 301 proximal the access gap 406. In a further embodiment, the sleeve advancing wire 503 is affixed at or near the end of the first sleeve 301 distal the access gap 406.

It is contemplated that, although the concepts of the present disclosure are illustrated with primary reference to the motor and wire configuration of FIGS. 1A and 1B, the access control mechanism 405 of the present disclosure may be operated with a variety of alternative actuation mechanisms. For example, it is contemplated that the access control mechanism 405 may employ direct or indirect actuation through the use of electrical, magnetic, capacitive, or other coupling sufficient to impart reciprocal or otherwise controllable movement to one or both of the sleeves 301, 302.

In an embodiment, the first and second sleeves 301, 302 of the access control mechanism 405 may be formed from elastic inert materials such as elastomers, elastic fibers, or rubbers. Non-limiting examples of the elastic inert materials include polypropylene, polyethylene, and polycarbonate. In general, any plastic material inert to organic solvents may be used to make the first and second sleeves 301, 302 of the access control mechanism 405. When the access control mechanism 405 is formed from elastic materials, the access control mechanism 405 can conform to the geometry of the working electrode 202. In this manner, the elastic materials of the first and second sleeves 301, 302 of the access control mechanism 405 facilitate formation of the fluid tight seal 408, 409 between the access control mechanism 405 and the working electrode 202. For example, if end faces of the first and second sleeves 301, 302 of the access control mechanism 405 including tight fitting slots or passages for accommodating passage of the working electrode 202 therethrough, the material of the end faces will be stretched radially when disposed on the working electrode 202, and the resulting compressive force of the stretched elastic material will form a seal against the working electrode 202. Alternative seal configurations, with or without compressive engagement of the sleeve material and the electrode, are contemplated.

Because electropolymerization occurs only at the working electrode 202, the use of a controlled access housing such as the access control mechanism 405 is generally applicable to only the working electrode 202. Though, for this reason, an access control mechanism would typically be unnecessary for the counter electrode 205 and the reference electrode 204, embodiments are contemplated in which the counter electrode 205, the reference electrode 204, or both could include an analogous type of access control mechanism.

The access control mechanism 405 allows the working electrode 202 to analyze multiple analyte samples with minimal downtime between each analysis. Specifically, the working electrode 202 is capable of multiple usages without its removal from the salt content analyzer 100. The electropolymerization process results in the working electrode 202 being coated with a layer of polymer. In the absence of an access control mechanism 405, the layer of polymer on the working electrode 202 would grow thicker after each analysis and would change the electrical characteristics of the working electrode 202. In order for an electrode to be operational and for electropolymerization to occur, the electrode surface generally must be clean and preferably even polished surface. A working electrode without an access control mechanism 405 would require cleaning and polishing after every analysis or determination to remove the layer of polymer formed during the previous analysis. The process of polishing requires removal of the electrode from the salt content analyzer 100, which is time consuming and results in analyzer downtime.

The working electrode 202 and the access control mechanism 405 ensure that only a limited portion of the working electrode 202 surface is exposed to the test fluid 206 at any given time, with the remainder of the working electrode 202 being concealed or covered by the access control mechanism 405. Prior to each analysis, an access area 404 of the working electrode 202 is exposed mechanically, so to enable electropolymerization to take place only within the access area 404. After the first such analysis, the area of the electrode that was exposed during the first analysis is covered, and a fresh polished electrode surface is made available for analysis of the subsequent analyte sample. Specifically, the access area 404 from the first analysis is concealed or covered by the access control mechanism 405 and simultaneously a fresh access area 404 is uncovered or exposed for utilization in a subsequent analysis. The access control mechanism 405 moves along the working electrode 202 so that as one portion of the working electrode 202 is concealed another portion of the working electrode 202 is uncovered or exposed. Specifically, different areas of the working electrode 202 are exposed after each analysis to create a fresh access area 404 for each later analysis.

In some embodiments, the total surface area of working electrode 202 exposed during each analysis may remain constant for each measurement; because the access control wires 304 maintain a constant length 412 of the access area 404. The total surface area of exposed working electrode 202 remains constant because the size of the access area 404 remains constant between tests, and the geometry of the working electrode 202 is consistent along the length. The total length of the working electrode 202 dictates the number of times the working electrode 202 can be used for analysis of salt content of the test fluid 206, which is related to the salt content in the analyte, in a sequential and serial manner without removal, cleaning, and polishing of the working electrode 202 between each analysis or determination. Analysis of salt content in the analyte in a serial manner means that multiple analyses may be performed in series with limited downtime between each analysis. In some embodiments, the access area 404 may be moved in a step-wise manner along the length of the working electrode 202 for each subsequent analysis, such that the total number of analyses that can be performed before working electrode 202 removal is necessary is related to the total usable length of working electrode 202 divided by the length of working electrode 202 exposed in the access area 404 for each analysis. Movement in a step-wise manner along the length of the working electrode 202 means that the access area 404 for each analysis does not overlap with the access area 404 of a previous analysis. In some embodiments the access area 404 of sequential analyses may abut on the working electrode 202. In other embodiments, a gap of unused electrode may be retained between the access area 404 provided in one analysis and the access area provided in subsequent analyses.

In principle, the changing of the access area 404 between each analysis ensures availability of a fresh working electrode 202 surface for deposition of a polymer film. In one embodiment a total of ten to twelve measurements of salt in an analyte can be measured in a serial manner using one working electrode 202. In other illustrative embodiments, the working electrode 202 has a length, and the access area has a length 412, both chosen so that approximately 5 analyses, approximately 10 analyses, approximately 20 analyses, or approximately 25 analyses can be made using a single working electrode without stopping to clean the working electrode 202 surface.

Once the entire surface of the working electrode 202 is used or consumed, the operator can remove the working electrode 202 and simply polish the entire surface. The re-polished working electrode 202 can thereafter be reinstalled in the access control mechanism 405 to be ready for the next round of serial use. This technique leads to continuous functioning of the salt content analyzer 100 without a need for polishing the working electrode 202 at the beginning of each measurement. The period of the controlled access operation depends on the demand of analysis and the length and the diameter of working electrode 202.

The salt content analyzer 100 may include three electrodes, which in combination allow the salt content of an analyte to be determined. The three electrodes are the working electrode 202, the reference electrode 204, and the counter electrode 205. In an embodiment, the working electrode 202 is a platinum electrode. Other non-limiting examples of working electrodes 202 include a glassy carbon electrode, a gold electrode, or a graphite electrode. In a further embodiment, the counter electrode 205 is a platinum electrode. Other non-limiting examples of counter electrodes 205 include a graphite electrode, a carbon paste electrode, a glassy carbon electrode, a gold electrode, or a hydrogen electrode. It is envisioned that in various embodiments the working electrode 202 and the counter electrode 205 are the same material while in other embodiments the working electrode 202 and the counter electrode 205 are different materials. In still further embodiments, the reference electrode 204 may be an Ag/AgCl electrode. Other non-limiting examples of reference electrodes 204 include a saturated calomel electrode, a hydrogen electrode, a graphite electrode, a platinum electrode, a gold electrode, or a glassy carbon electrode.

The analysis vessel 22 contains the three electrodes and is the site of analysis of analyte samples. The analyte and the various reagents used to determine the salt content of the analyte are combined in the analysis vessel 22. In an embodiment, the analysis vessel 22 is formed from or lined with an inert material that will not react with the various reagents or analytes which are disposed therein to form the test fluid 206 on which the analysis is performed. Non-limiting examples of the inert material include an inert glass, an inert plastic, or an inert ceramic.

In a further embodiment, the analysis vessel 22 includes a stirrer 203. The stirrer 203 may be included in the analysis vessel 22 to ensure complete mixing of the analyte and various reagents which are combined in the analysis vessel 22 to form the test fluid 206. Non-limiting examples of the stirrer 203 include a mechanical device or a magnetic bar. When the stirrer 203 is a magnetic bar, the salt content analyzer 100 may be placed over a magnetic stifling plate that spins the magnetic bar during an analysis.

Figure 3:
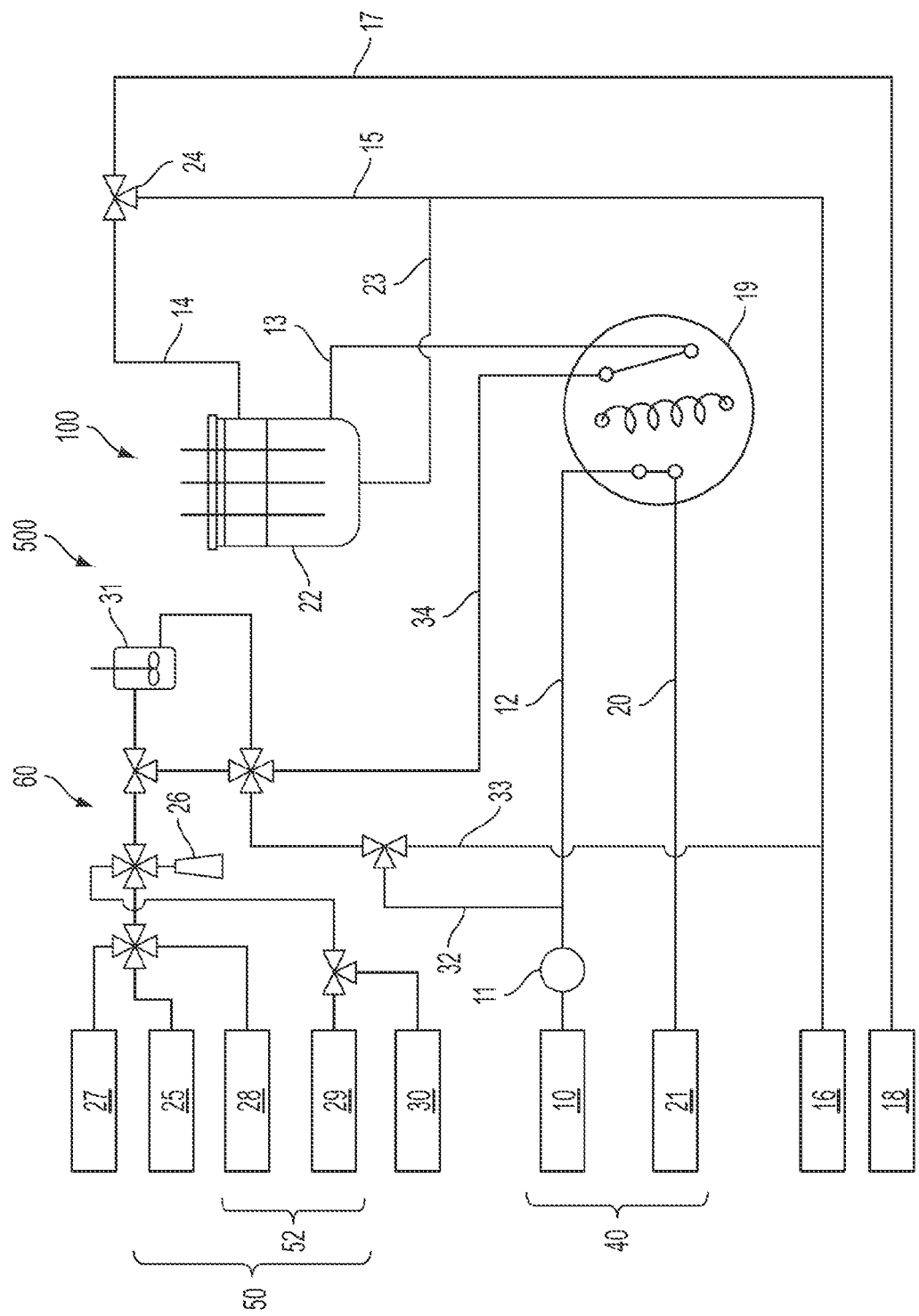
FIG. 3 is a schematic representation of an analysis system including a salt content analyzer, according to embodiments described herein.

Referring to FIG. 3, an analysis system 500 which includes a salt content analyzer 100 is shown. In an embodiment, the salt content analyzer 100 includes an analyte metering system 40 which includes a sampling line 10, a sampling pump 11, and a sampling valve 19. The volume of analyte provided to the analysis vessel 22 for testing should be precisely and accurately measured. Precision and accuracy in the volume of analyte sample tested is important because the volumes of solvents added to the analyte sample are determined in accordance to the volume of analyte. If too much analyte is added relative to the volume of solvents the analysis will provide an artificially high and incorrect salt concentration. Conversely, if too little analyte is added relative to the volume of solvents the analysis will provide an artificially low and incorrect salt concentration. It is imperative that the volume of analyte and solvents mixed together to form test fluid 206 are precisely known to allow calculation of the final salt concentration. In an embodiment, the sampling line 10 is connected to the analyte source to be monitored and tested. For example, the sampling line 10 may be connected to the exit stream from a desalination process in a refinery. In such an example, the sampling line 10 would extract a sample of the analyte from the exit stream for subsequent testing in the salt content analyzer 100. In accordance with an embodiment, the sampling pump 11 provides a locomotive force that directs the analyte for testing through the analyte metering system 40. The sampling valve 19 injects the correct volume of analyte into the analysis vessel 22. Specifically, the sampling valve 19 may include a loop that allows precisely a predetermined quantity or volume of analyte to dispense into the analysis vessel 22. The volume is based on the loop size of the sampling valve 19.

In an embodiment, the salt content analyzer 100 includes a solvent supply 50 which includes a water supply 25 and at least one conductivity solvent supply 52. The water supply 25 and the conductivity solvent supply 52 are connected to a water source and at least one conductivity solvent source respectively to provide the water and conductivity solvents that are mixed with the analyte and electro-polymerizable monomer for analysis. In an embodiment, the conductivity solvent supply 52 includes at least one of a N-methylpyrrolidone source 29, a methanol source, a methyl tert-butyl ether source, and/or an acetonitrile source 28 to provide N-methylpyrrolidone, methanol, methyl tert-butyl ether, and/or acetonitrile respectively. Other non-limiting examples of conductivity solvents include dimethylformamide; 2,5-dimethoxytetrahydrofuran; tetrahydrofuran; nitrobenzene; dimethyl sulfoxide; tributyl phosphate; trimethyl phosphate; propylene carbonate; nitromethane; chlorobenzene; anisole; γ-butyrolactone; ethanol; propanol and dichloromethane. In a further embodiment, the conductivity solvent supply 52 includes a N-methylpyrrolidone source 29 to provide N-methylpyrrolidone and an acetonitrile source 28 to provide acetonitrile. Each of the N-methylpyrrolidone source 29, the methanol source, the methyl tert-butyl ether source, and the acetonitrile source 28 are a vessel that contains an amount of the respective conductivity solvent necessary to run the analysis system 500.

The electro-polymerizable monomer supply 27 provides the electro-polymerizable monomer for flow into the analysis vessel 22. The electro-polymerizable monomer supply 27 provides electro-polymerizable monomer from an electro-polymerizable monomer source. The electro-polymerizable source is a vessel containing an amount of electro-polymerizable monomer necessary to run the analysis system 500 and the salt content analyzer 100. Non-limiting examples of the electro-polymerizable monomer include aniline; thiophene; benzo-thiophene; dibenzothiophene; pyridine; acetylene; acrylonitriles, including methyl acrylonitrile; anilines, including derivatives bearing sulpho, carboxyl and hydroxyl functional groups; azulene; mono-carbazoles, including vinyl carbazole, N-carbazole and monoethyl-carbazole; dicarbazoles, including 2,6-bis-carbazol-9-yl-hexanoic acid pentafluorophenyl ester, 2,6-bis-carbazol-9-yl-hexanoic acid 2,5-dioxo-pyrrolidin-1-yl ester, 2,6-bis-carbazol-9-yl-hexanoic acid 1,3-dioxo-1,3-dihydro-isoindol-2-yl ester, 2,6-bis-carbazol-9-yl-hexanoic acid methyl ester, 2,6-bis-carbazol-9-yl-hexanoic acid, 2,6-bis-carbazol-9-yl-hexan-1-ol acetate, 2,6-bis-carbazol-9-yl-chlorohexane and 2,6-bis-carbazol-9-yl-hexan-1-ol; tetrathiafulvalene; naphthalenes, including diaminonaphthalene; indole; pyrroles, including N-substituted pyrroles, N-functionalized pyrroles, N-methyl-N'-(6-pyrrol-1-ylhexyl)-4,4'-bipyridinium dihexafluorophosphate and N,N'-bis(6-pyrrol-1-ylhexyl)-4,4'-bipyridinium dihexafluorophosphate; thiophenes, including 2,2'-bithiophene, 3-methyl thiophene, 3-bromothiophene, 3,4-dibromo thiophene, 3,4-dimethylthiophene, 3,4-methyl ethyl thiophene, 3,4-diethyl thiophene, 3-thiomethyl thiophene, benzo-thiophene and dibenzo-thiophene; phenyl quinolone; phenylenes, including para-phenylene, para-phenylene vinylene and phenylene sulfide; pyridine; acrylates, including methyl methacrylate and ethyl acrylate; styrene; and vinyl-metallo monomers, which are vinyl monomers with organometallic side units that form polyvinyl metallo polymers upon electropolymerization. One of ordinary skill in the art understands that suitable electropolymerizable monomers also include all derivatives of the monomer species identified as well as other electropolymerizable monomers not identified but suitable for electrochemical polymerization processes in hydrocarbon-based solutions.

In an embodiment, the salt content analyzer 100 also includes a reagent metering system 60 that transports each of the various reagents utilized as part of the analysis of the salt content of an analyte sample to the analysis vessel 22. The reagents transported by the reagent metering system include, but are not limited to, distilled deionized water, electro-polymerizable monomer, and conductivity solvents. A series of valves and a digital syringe 26 direct flow of each reagent and precisely measure the required amount of each reagent for mixing with the analyte.

In an embodiment, the test fluid 206 comprises approximately 10 wt % electro-polymerizable monomer, approximately 90 wt % solvents, and a trace amount of analyte. A specific, non-limiting, example of the ratio of constituents of the test fluid 206 is approximately $2 \times 10^{-5}$ wt % analyte, approximately 9.1 wt % electro-polymerizable monomer, and approximately 90.9 wt % solvents.

The salt content analyzer 100 may further include a voltage source such as a potentiostat-galvanostat instrument capable of controlling a sweeping of electrical voltages. The electro-polymerizable monomer initiates polymerization at a monomer specific polymerization voltage. Application of a sweeping of electrical voltage initiates polymerization of the electro-polymerizable monomer as the monomer specific polymerization voltage is passed during a voltage sweeps. In illustrative embodiments, the electrical voltage is swept between approximately 0 V and approximately 3 V. The rate of voltage sweep in various embodiments is approximately 10 mV/s. In further embodiments, the rate of voltage sweep is approximately 1 mV/s, approximately 5 mV/s, approximately 8 mV/s, approximately 12 mV/s, or approximately 15 mV/s.

The electro-polymerizable monomers each have a specific voltage at which the monomer polymerizes. For example, aniline is polymerized at approximately 1.9 V. The specific electro-polymerization voltages for various other electro-polymerizable monomers are known or are obtainable by one of skill in the art without undue experimentation.

While the potentiostat-galvanostat instrument applies the sweeping of electrical voltages, the corresponding current may be recorded by a measurement apparatus, for example. The final output of the sweeping of electrical voltages provides a cyclic voltammogram of current versus voltage. Once potential is applied at the specific polymerization voltage across the working and counter electrode 205, a thin film of electro-polymerized monomer begins to be deposited on the working electrode 202. The amount of electro-polymerized monomer film deposited over the time period of the voltage sweep is dependent on the amount of salt present in the matrix. Once polymerization begins to occur and the polymer layer forms on the working electrode 202, the resistance of the system increases, because the growing polymer layer adds a progressively increasing resistance. In accordance with Ohm's law (voltage (V)=current (I) times resistance (R)), once polymerization begins to occur on the working electrode 202 and resistance of the system increases, the current begins to drop. Thus, the peak current of the cyclic voltammogram represents the voltage at which polymerization takes place. The quantity of polymer formed from the electro-polymerizable monomer in the test fluid upon application of the electrical potential is directly proportional to the amount of electrolyte present in the test fluid 206, which directly correlates to the salt content of the analyte. Thus, the peak current is directly proportional to the salt content of the analyte. Using a calibration curve generated from analyte samples having known salt concentrations, the unknown salt concentration of an analyte sample can be obtained based on the peak current measured during an analysis using the salt content analyzer 100. The peak current is proportional to the amount of salt present in the analyte because increased salt reduces the resistance of the test fluid 206. A reduction in resistance generates an increased current for a given voltage.

Figure 4:
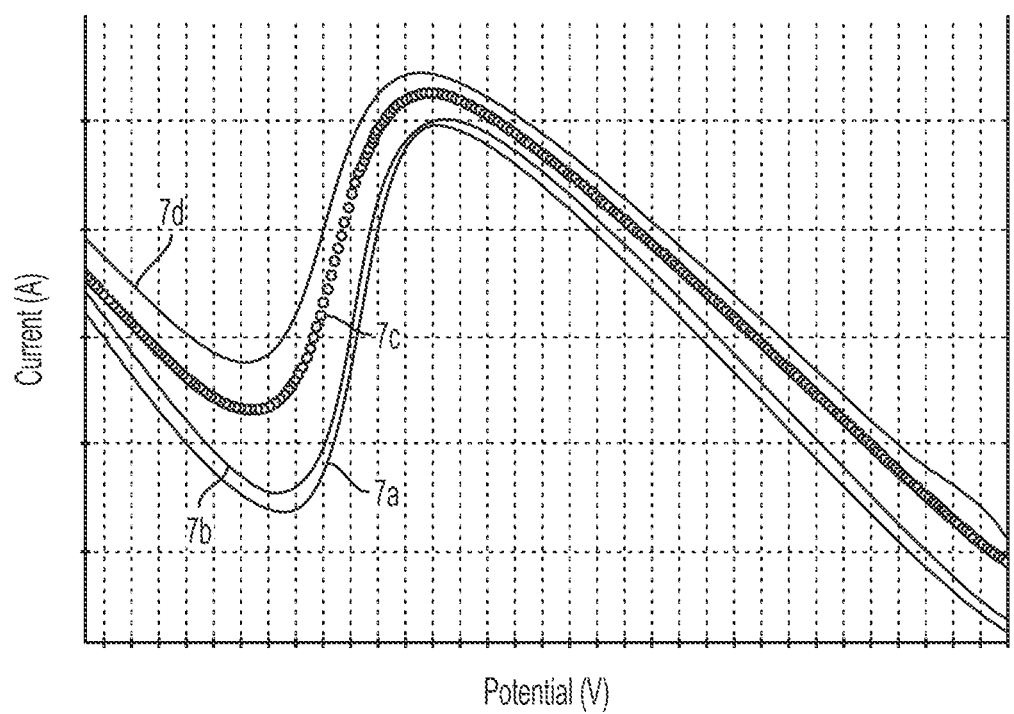
FIG. 4 is a cyclic voltammogram of varying salt concentrations in the same base analyte sample.

Referring to FIG. 4, cyclic voltammograms of electro-polymerization of analytes with different salt contents is shown. The cyclic voltammogram in FIG. 4 has four traces generated of current during electro-polymerization. Each trace corresponds to a different salt content being present in the same base analyte. The x-axis represents applied potential in voltage, and the y-axis represents current produced in µA. Trace 7a represents the analyte with the lowest salt content. Trace 7d represents the analyte with the highest salt content. Traces 7b and 7c represent analytes with intermediate concentrations of salt. The results generated in FIG. 4 are obtained using the same paraffin matrix obtained from the same reservoir and subsequently seeding the paraffin matrix with varying amounts of salt.

The salt content analyzer 100 determines a salt concentration independent of temperature variation because electrochemical polymerization is altered by only the applied potential. The salt content analyzer 100 is not affected by corrosion or precipitation on the electrodes, because the working electrode 202 is regenerated for each test by adjusting the access control mechanism 405 to reveal a fresh access area 404 for use in testing.

In an embodiment the analyzer further includes a purge gas supply 18. The purge gas supply 18 provides a purge gas that may be routed through the salt content analyzer 100 subsequent to testing of an analyte sample to flush out the used test fluid 206 and residual analyte in preparation for determination of salt content of another analyte sample.

In an embodiment the analyzer further includes a cleaning solvent supply 30. The cleaning solvent supply 30 provides a cleaning solvent that may be routed through the salt content analyzer 100 subsequent to testing of an analyte sample to clean the system in preparation for determination of salt content of another analyte sample.

Having described above several embodiments of the salt content analyzer 100, various embodiments of methods for determining the salt content of a petroleum product using the salt content analyzer will now be described. In some embodiments, the methods for determining the salt content of a petroleum product may be performed using the salt content analyzer 100 of FIGS. 1-3 according to embodiments described above.

FIG. 3 represents a schematic of an analysis system 500 including a salt content analyzer 100. An analyte sample from sampling line 10 is pumped thru sampling pump 11 using sample-in line 12 and is allowed to pass thru the sampling valve 19. Any extraneous analyte that is not diverted by the sampling valve 19 may be allowed to leave through sample out line 20 to sample outlet 21. Under valve-on conditions the analyte flows through a loop in the sampling valve 19 and the predetermined quantity of analyte is dispensed into analysis vessel 22 through sample line 13. A calculated amount of a conductivity solvent, for example N-methylpyrrolidone from the N-methylpyrrolidone source 29, using digital syringe 26, is added to analysis vessel 22. Calculated amounts of electro-polymerizable monomer from the electro-polymerizable monomer supply 27 using digital syringe 26 and acetonitrile from the acetonitrile source 28 are dispensed into analysis vessel 22 utilizing sample lines and mixer 31. Water, such as distilled deionized water, from the water supply 25 is also added to analysis vessel 22 using the various valves, mixer 31, and sample lines 34 and 13. Accuracy of the volume water from the water supply 25 added to the analysis vessel 22 is measured by digital syringe 26. After the first sample is analyzed, the test fluid 206 in analysis vessel 22 is drained through sample lines 23 and 15 to drain valve 16.

In a further embodiment, a purge gas from purge gas supply 18 flows thru sample line 17, using solenoid valve 24 and is allowed to flow thru sample line 14 so that the analysis vessel 22 is cleaned. To clean the drain line 15, purge gas from purge gas supply 18 is routed using solenoid valve 24 to send the purge gas thru sample line 15. In still a further embodiment, a cleaning solvent from cleaning solvent supply 30 is allowed to pass through all the sample lines, the digital syringe 26, the mixer 31, the six-port sampling valve 19, the analysis vessel 22, and all valves.

In principle, embodiments of methods for determining the salt content of a petroleum product are capable of detecting inorganic salts (such as sodium chloride, potassium chloride, sodium nitrate, magnesium chloride, in general salts of alkali and alkaline earth metals) present in an analyte such as paraffin oil, crude oil, gasoline, diesel fuel, or similar high electrical resistivity fluid. The sampling and valve system are configured to prepare a reliable and representative sample of the analyte, in addition to mixing of different solvents to enhance conductivity of the analyte sample and optimization of the electro-chemical polymerization.

It should be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A salt content analyzer that performs multiple sequential determinations of a salt content of an analyte in a test fluid comprising the analyte and an electro-polymerizable monomer without requiring intermediate cleaning or polishing of a working electrode between determinations, the salt content analyzer comprising:
- an analysis vessel that accommodates the test fluid, a counter electrode, and a reference electrode;
- a working electrode assembly comprising the working electrode and an access control mechanism, the working electrode assembly being immersible in the test fluid; and a voltage source that applies an electrical potential to the working electrode;
- a measurement apparatus that measures an electrical current passed between the working electrode and the counter electrode when the electrical potential is applied to the working electrode;

wherein:
- the working electrode and the counter electrode form an electrochemical cell;
- the access control mechanism of the working electrode assembly comprises a movable barrier that exposes a measuring portion of the working electrode to the test fluid through an access gap and forms a fluid tight seal around a covered portion of the working electrode, the fluid tight seal preventing exposure of the covered portion to the test fluid;
- during a single determination of the analyte in the test fluid, electropolymerization of the electro-polymerizable monomer occurs at the measuring portion of the working electrode and a polymer film is deposited onto the measuring portion to form a used measuring portion;
- after the single determination, movement of the movable barrier exposes a fresh measuring portion of the working electrode for use in a subsequent determination without requiring intermediate cleaning or polishing of the working electrode and forms the fluid tight seal around the used measuring portion formed during the single determination.

2. The salt content analyzer of claim 1, wherein the access control mechanism comprises a first sleeve and a second sleeve disposed over opposite ends of the working electrode and extending lengthwise over the covered portion of the working electrode, each of the first sleeve and the second sleeve having a proximal end, the proximal ends of the first sleeve and the second sleeve defining the access gap between the proximal ends of the first sleeve and the second sleeve, the measurement portion of the working electrode being exposed to the test fluid through the access gap.

3. The salt content analyzer of claim 2, wherein the sleeves comprise an elastomer.

4. The salt content analyzer of claim 3, wherein the elastomer is polypropylene, polyethylene, or polycarbonate.

5. The salt content analyzer of claim 2, wherein the first sleeve and the second sleeve are connected by a plurality of access control wires that maintain the access gap at a constant width between the proximal ends of the first sleeve and the second sleeve.

6. The salt content analyzer of claim 1, wherein salt content analyzer further comprises a reagent metering system comprising a digital syringe that measures amounts of the test fluid provided to the analysis vessel, a mixer that stirs the test fluid in the analysis vessel, and a plurality of valves that provide the test fluid to the analysis vessel.

7. The salt content analyzer of claim 6, wherein the salt content analyzer further comprises a solvent supply that provides water and at least one conductivity solvent to the reagent metering system, the at least one conductivity solvent chosen from N-methylpyrrolidone, methanol, methyl-tert-butyl ether, acetonitrile, and mixtures thereof.

8. The salt content analyzer of claim 6, wherein the salt content analyzer further comprises a solvent supply that provides water and at least two conductivity solvents to the reagent metering system, the at least two conductivity solvents comprising N-methylpyrrolidone and acetonitrile.

9. The salt content analyzer of claim 6, wherein the salt content analyzer further comprises an analyte metering system that provides the analyte to the reagent metering system, the analyte being chosen from crude oil, paraffin oil, gasoline, or diesel fuel.

10. The salt content analyzer of claim 1, wherein the working electrode is a platinum electrode, a glassy carbon electrode, or a graphite electrode.

11. The salt content analyzer of claim 1, wherein the electro-polymerizable monomer is aniline, thiophene, benzothiophene, dibenzothiophene, or pyridine.

12. The salt content analyzer of claim 1, wherein the analysis vessel comprises an inert glass, an inert plastic, or an inert ceramic.

13. The salt content analyzer of claim 1, wherein the analysis vessel comprises a stirrer that stirs the test fluid in the analysis vessel during the multiple sequential determinations.

14. The salt content analyzer of claim 1, wherein the salt content analyzer further comprises a purge gas supply that provides a purge gas for flushing out the salt content analyzer between determinations.

15. The salt content analyzer of claim 1, wherein the salt content analyzer further comprises a cleaning solvent supply that provides a cleaning solvent for cleaning the salt content analyzer between determinations.

16. A method of performing multiple sequential determinations of salt content in a petroleum product without intermediate cleaning or polishing of a working electrode between determinations, the method comprising:
- providing a salt content analyzer having an analysis vessel, a working electrode assembly comprising a working electrode and an access control mechanism, a voltage source, and a measurement apparatus, the access control mechanism of the working electrode assembly comprising a movable barrier that exposes a measuring portion of the working electrode through an access gap to a test fluid containing the petroleum product in the analysis vessel and forms a fluid tight seal around a covered portion of the working electrode, the fluid tight seal preventing exposure of the covered portion to the test fluid;
- mixing the petroleum product and a homogenous mixture to the analysis vessel to form the test fluid, the homogeneous mixture comprising water, at least one conductivity solvent, and at least one electro-polymerizable monomer;
- applying a sweeping potential with the voltage source to the working electrode in the test fluid to generate an electric current from a counter electrode in the test fluid to the working electrode, whereby electropolymerization of the electro-polymerizable monomer occurs at the measuring portion of the working electrode and a polymer film is deposited onto the measuring portion to form a used measuring portion;
- recording with the measurement apparatus a peak current generated during the application of the sweeping potential;
- comparing the peak current with a predetermined calibration curve to determine the salt content of the petroleum product; and moving the movable barrier of the access control mechanism to cover the used measuring portion of the working electrode and to expose a fresh measuring portion of the working electrode for use in a subsequent determination.

17. The method of claim 16, further comprising:
draining the analysis vessel after the peak current is recorded;
supplying a purge gas to the drained analysis vessel to remove any remaining test fluid in the analysis vessel; and
performing a subsequent determination of salt content of an additional test fluid while the fresh measuring portion of the working electrode is exposed.

18. The method of claim 16, further comprising:
draining the analysis vessel;
supplying a cleaning solvent to the drained analysis vessel to clean the analysis vessel; and
performing a subsequent determination of salt content of an additional test fluid while the fresh measuring portion of the working electrode is exposed.

19. The method of claim 16, further comprising performing multiple subsequent determinations of salt contents of test fluids containing the petroleum product until the movable barrier reaches an end of the working electrode and no additional fresh measuring portion can be exposed by the movement of the movable barrier.

20. An analyzer comprising:
an analysis vessel that accommodates a test fluid, a counter electrode, and a reference electrode;
a working electrode assembly comprising a working electrode and an access control mechanism, the working electrode assembly being immersible in the test fluid; and
a voltage source that applies an electrical potential to the working electrode;
a measurement apparatus that measures an electrical current passed between the working electrode and the counter electrode when the electrical potential is applied to the working electrode;
wherein:
the working electrode and the counter electrode form an electrochemical cell;
the access control mechanism of the working electrode assembly comprises a movable barrier that exposes a measuring portion of the working electrode to the test fluid through an access gap and forms a fluid tight seal around a covered portion of the working electrode, the fluid tight seal preventing exposure of the covered portion to the test fluid; and
movement of the movable barrier exposes a fresh measuring portion of the working electrode.

* * * * *